(12) United States Patent
Braun

(10) Patent No.: US 8,015,861 B2
(45) Date of Patent: Sep. 13, 2011

(54) ARTICLE AND METHOD FOR STABILIZING A ROCK CHIP

(75) Inventor: Gerald E. Braun, Magnolia, TX (US)

(73) Assignee: Baker Hughes Incorporated, Houston, TX (US)

( * ) Notice: Subject to any disclaimer, the term of this patent is extended or adjusted under 35 U.S.C. 154(b) by 472 days.

(21) Appl. No.: 12/359,050

(22) Filed: Jan. 23, 2009

(65) Prior Publication Data

US 2010/0186488 A1    Jul. 29, 2010

(51) Int. Cl.
*G01N 3/48* (2006.01)
(52) U.S. Cl. .......................................................... 73/81
(58) Field of Classification Search ............... 73/81, 244, 73/356, 856
See application file for complete search history.

(56) References Cited

U.S. PATENT DOCUMENTS

| 4,956,994 A | * | 9/1990 | Lue | 73/81 |
| 6,142,010 A | * | 11/2000 | Merck et al. | 73/81 |

* cited by examiner

*Primary Examiner* — Lisa Caputo
*Assistant Examiner* — Jamel Williams
(74) *Attorney, Agent, or Firm* — R. Andrew Patty, II; McGlinchey Stafford, PLLC

(57) ABSTRACT

An article and method for stabilizing a rock chip. The article in one embodiment of the invention includes a laminar rock chip substantially surrounded by and imbedded within a plug having a solid material, the plug forming a top planar surface and a bottom planar surface substantially parallel with the top planar surface, the laminar rock chip forming a contact surface portion exposed at the top planar surface of the plug, a laminar plane of the laminar rock chip being substantially perpendicular with the top planar surface.

29 Claims, 1 Drawing Sheet

ARTICLE AND METHOD FOR STABILIZING A ROCK CHIP

TECHNICAL FIELD

This invention relates to an apparatus or article and related method useful in stabilizing solid material, and in particular stabilizing laminar rock chips being analyzed for hardness.

BACKGROUND

In preparing for the stimulation of production of oil and gas wells, e.g., hydraulic fracturing, observing and testing core samples provide operators with useful geologic information regarding the formation through which the well bore is formed. An operator at the well site may collect the core samples and either perform field tests or send the samples to an off-site location for analysis. When analyzing the samples, different properties of the rock may be determined, including the hardness of the rock. In order to test the hardness of a rock, typically a technician will place the rock sample in a hardness tester and apply an indenter to the surface of the rock sample parallel to the laminar plane of the rock sample to determine the hardness of the rock sample. Typical rocks found in production stimulation include sandstone, limestone, shale, dolomite, and the like.

SUMMARY OF THE INVENTION

Due to the physical characteristics of shale rock, the shale rock chips from the core samples are typically small, thin, and sliver-type in shape and form. Thus, in performing the above hardness tests on shale, a problem has been determined to exist in that the properties of the individual shale rock chips, including the size and shape, do not allow for the placement of the individual shale rock chips in a hardness tester such that the technician can effectively apply an indenter to the surface of the rock sample parallel to the laminar plane of the rock sample to determine the hardness of the rock sample. It has now become apparent that a need exists for an apparatus and method for stabilizing rock chips when measuring physical characteristics, including the hardness of a particular rock chip. Specifically, this need is particularly acute when measuring the hardness of a shale rock chip upon retrieval from a well bore. Due to the physical characteristics of the shale rock chips, the technician attempting to measure the hardness of the rock chip sample is currently unable to use a traditional hardness testing device, such as a Brinell hardness tester, for example.

The present invention is deemed to meet the foregoing need, amongst others, by providing in at least one embodiment, an article comprising at least one laminar rock chip substantially surrounded by and imbedded within a plug comprised of a solid material, the article capable of being placed in a hardness tester so that the hardness of the laminar rock chip may be measured. In at least one embodiment of the invention, the laminar rock chip is imbedded in the plug such that the laminar plane of the laminar rock chip is parallel to the direction of the ball indenter and, thus, capable of an accurate hardness measurement.

In an embodiment of this invention, provided is a method which comprises disposing a retention member adjacent a planar surface. The retention member forms one or more inner side walls which, together with the planar surface, define a retention member void sized to receive a laminar rock chip. The method further comprises disposing the laminar rock chip in the retention member void such that a laminar plane of the laminar rock chip is substantially perpendicular to the plane of the planar surface and placing into the retention member void a flowable material capable of hardening. The flowable material flows between a bottom surface of the laminar rock chip and the planar surface and further flows around the laminar rock chip such that substantially all of the surface area of the laminar rock chip is covered by the flowable material. The method further comprises causing the flowable material to harden into a solid while retaining the laminar rock chip in place so that the laminar plane of the laminar rock chip remains substantially perpendicular to the plane of the planar surface, thereby forming a plug of solid material having the laminar rock chip embedded therein, and removing the plug from the planar surface and abrading a top surface of the plug, the top surface and a bottom surface of the plug being substantially parallel to one another. The top surface is sufficiently abraded so that a contact surface portion of the laminar rock chip is exposed at the top surface. The method also comprises placing the bottom surface of the plug upon a hardness testing device support plate and contacting the contact surface portion of the laminar rock chip at the top surface with a primary contact member of the hardness testing device so that force is applied by the primary contact member to the contact surface portion of the laminar rock chip in a vector which is within the laminar plane of the laminar rock chip, so that a hardness of the laminar rock chip is measured.

Another embodiment of this invention is an article comprising a laminar rock chip substantially surrounded by and imbedded within a plug comprised of a solid material. The plug forms a top planar surface and a bottom planar surface substantially parallel with the top planar surface. The laminar rock chip forms a contact surface portion exposed at the top planar surface of the plug. A laminar plane of the laminar rock chip is substantially perpendicular with the top planar surface.

In yet another embodiment of the present invention, provided is a method comprising disposing a retention member adjacent a planar surface. The retention member forms one or more inner side walls which, together with the planar surface, define a retention member void sized to receive a laminar rock chip. The method further comprises disposing the laminar rock chip in the retention member void and placing into the retention member void a flowable material capable of hardening. The flowable material flows between a bottom surface of the laminar rock chip and the planar surface and further flows around the laminar rock chip such that substantially all of the surface area of the laminar rock chip is covered by the flowable material. The method further comprises causing the flowable material to harden into a solid while retaining the laminar rock chip in place, thereby forming a plug of solid material having the laminar rock chip embedded therein, and removing the plug from the planar surface and abrading a top surface of the plug, the top surface and a bottom surface of the plug being substantially parallel to one another. The top surface is sufficiently abraded so that a contact surface portion of the laminar rock chip is exposed at the top surface. The method further comprises placing the bottom surface of the plug upon a hardness testing device support plate and contacting the contact surface portion of the laminar rock chip at the top surface with a primary contact member of the hardness testing device so that force is applied by the primary contact member to the contact surface portion of the laminar rock chip, so that a hardness of the laminar rock chip is measured.

Still yet, another embodiment of the present invention is an article comprising a laminar rock chip substantially surrounded by and imbedded within a plug comprised of a solid material. The plug forms a top planar surface and a bottom planar surface substantially parallel with the top planar surface, the laminar rock chip forming a contact surface portion exposed at the top planar surface of the plug.

These and other features of this invention will be still further apparent from the ensuing description, drawings, and appended claims.

FURTHER DETAILED DESCRIPTION OF THE INVENTION

Figure 1:
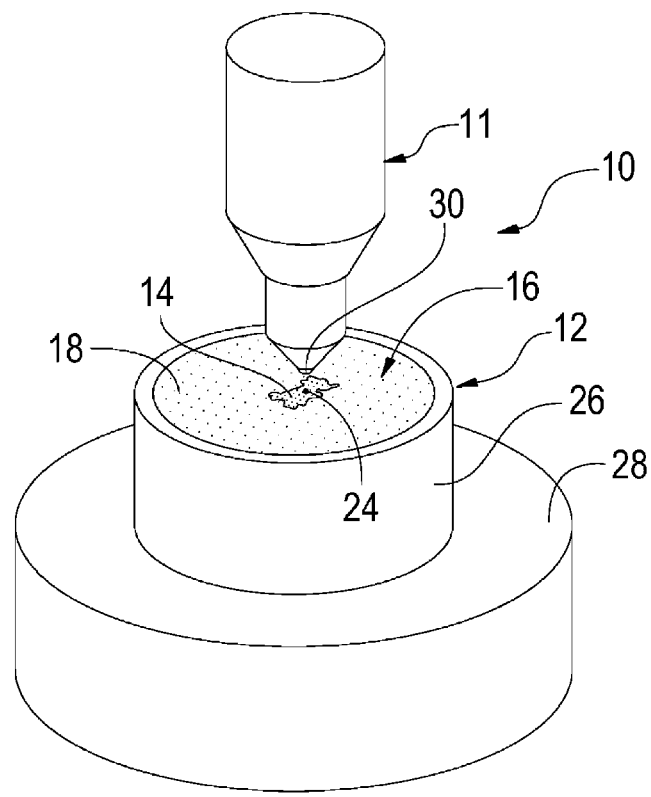
FIG. 1 is a perspective view of a plug, including a solid, a laminar rock chip, and a retention member, and a ball indenter consistent with one embodiment of the present invention.

Illustrative embodiments of the invention are described below as they might be employed in the construction and use of an apparatus for stabilizing a rock chip and methods according to the present invention. In the interest of clarity, not all features of an actual implementation are described in this specification. It will be of course appreciated that in the development of such an actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In one embodiment of this invention, a method for stabilizing a rock chip is provided. The method comprises disposing a retention member on a planar surface. The retention member forms one or more inner side walls which, together with the planar surface upon which the retention member rests, define a retention member void sized to receive a laminar rock chip. The retention member may be any component or device with a thickness, which along with the planar surface defines a void or chamber capable of receiving a laminar rock chip and also forming a substantially sealed chamber such that a flowable material as further defined below may be contained in the chamber or void without loss of the flowable material from the chamber. In one embodiment, the retention member is a metal ring approximately one to two millimeters in thickness and approximately one inch (2.54 centimeters) in diameter. However, the size and composition of the retention member may vary based on the nature of the flowable material placed in the retention member and the size and form of the rock chip placed therein. Suitable nonlimiting examples of retention members may include metal rings, a section of PVC piping, electrical conduit, plastic discs, and the like. The retention member comprises a top surface and a bottom surface and is typically machined or flattened on each the top surface and the bottom surface prior to placing the retention member on the planar surface. The retention member is machine or flattened so that the top surface is substantially parallel to the bottom surface.

The planar surface upon which the retention member is placed in accordance with this invention may be a glass plate; however, the planar surface alternatively may be any flat surface capable of creating a substantially sealed relationship with the bottom surface of the retention member. In one particular embodiment of this invention, either the top surface or the bottom surface of the retention member is coated with a silicon grease (e.g., VASELINE® ointment) before disposing the surface coated with grease on the planar surface. The plane of the planar surface may be defined as an imaginary plane parallel with and substantially occupied by the planar surface. In an alternate embodiment, the planar surface and the retention member may be parts of an integral unit, e.g., a mold.

A laminar rock chip is disposed in the retention member void such that a laminar plane of the laminar rock chip is substantially perpendicular to the plane of the planar surface. In one embodiment, the laminar rock chip is a shale rock chip. Although a shale rock chip is commonly tested, any type of rock chip may be disposed in the retention member void. Suitable nonlimiting examples of rock chips include shale, sandstone, limestone, dolomite, and the like. The laminar plane of the laminar rock chip is an imaginary plane parallel to and substantially occupied by at least one sedimentary layer of the laminar rock chip. In order to dispose the laminar rock chip substantially perpendicular to the plane of the planar surface, the laminar rock chip may be placed adjacent to a stabilizing member, wherein the stabilizing member comprises at least one support member. The stabilizing member retains the laminar rock chip such that the laminar plane of the laminar rock chip is substantially perpendicular to the plane of the planar surface. In one embodiment, the stabilizing member used is a metal clip from Buehler Corporation, of Lake Bluff, Ill. The stabilizing member comprises at least one support member, wherein the support member may be an arm or extension capable of supporting and holding at least a portion of the laminar rock chip. Stabilizing member may be made from a variety of materials; typically, the stabilizing member comprises plastic or metal. Stabilizing member may take the form of a "W" in shape and allow for the support of two or more laminar rock chips.

It should be appreciated that a sedimentary rock such as shale, sandstone, limestone, dolomite, and the like comprises at least one lamination and, typically, multiple laminations and as such may be defined as a laminar rock. However, it will be appreciated that the rock chip may be of a shape or form that only one lamination is present. This may most typically occur in rock other than shale rock, Preferably, when the rock chip comprises two or more laminations, i.e., layers, the laminar plane of the rock chip will be substantially perpendicular to the planar surface in the practice of the invention. Additionally, any rock chip comprising only one lamination may be orientated in any direction with respect to the planar surface during formation of the plug.

In at least one embodiment, a flowable material capable of hardening is placed into the retention member void. The flowable material flows between a bottom surface of the laminar rock chip and the planar surface and further flows around the laminar rock chip such that substantially all of the surface area of the laminar rock chip is covered by the flowable material. In one embodiment, a portion of the flowable material is placed within the retention member void before the laminar rock chip and stabilizing member are placed in the void. After a portion of the flowable material is placed in the void, the laminar rock chip and stabilizing member are placed in the void and the remainder of the flowable material is added to the void.

The flowable material may be any material capable of hardening into a solid. Such nonlimiting examples include epoxies, metal alloys, plastics, and powders. Some flowable material such as the plastics, metal alloys, and powders may be solids initially and subjected to heating and/or pressure to become flowable material. Flowable material may be defined as a material in a fluid state. With regards to metal alloys, particular nonlimiting examples include alloys of tin, bismuth, lead, cadmium, and/or indium. Particularly desirable characteristics of the metal alloys include low melting points and high tensile strength such that the flowable material does not shrink. Particularly desirable is a metal alloy having a melting point below 72° C. In one embodiment, the metal alloy OSTALLOY® 158 is used. In order to create a flowable material from the metal alloy, the metal alloy is exposed to a propane torch until the metal alloy changes state to a flowable material. With regards to epoxies used, particularly desirable characteristics of the epoxy includes a viscosity low enough to bond sufficiently to surface of the rock chip, but high enough so that the epoxy does not flow into the pores of the rock chip and artificially harden the rock chip, thereby skewing the natural hardness of the rock chip. In one embodiment, the epoxy used is EPO-KWIK, an epoxy made by the Buehler Corporation of Lake Bluff, Ill. The epoxy cures by exposure to atmospheric conditions. In one embodiment, Vaseline® or other suitable silicone grease may be applied to the inner side walls of the retention member in order to aid in the separation of the flowable material and the retention member after the flowable material has hardened into a solid.

In at least one embodiment, the flowable material hardens into a solid while retaining the laminar rock chip in place so that the laminar plane of the laminar rock chip remains substantially perpendicular to the plane of the planar surface, thereby forming a plug of solid material having the laminar rock chip embedded therein. The plug will be shaped in the form of the retention member used. In at least one embodiment, the plug is circular in shape and form.

The plug is removed from the planar surface by separating the plug from the planar surface. The plug comprises a top surface and a bottom surface. The top surface of the plug is abraded so that a contact surface portion of the laminar rock chip is exposed at the top surface. The bottom surface of the plug is then abraded so that the surfaces are substantially parallel to one another. Surfaces may be abraded by various means. In at least one embodiment, the plug is subjected to and abraded by manual or machine sanding using a series of abrasive papers (80-400 grit). Those of ordinary skill in the art will appreciate other means to abrade the surfaces of the plug, such as a rotating diamond impregnated plate. In at least one embodiment wherein epoxy is used as the flowable material, the plug and retention member are further separated from each other.

A hardness testing device is used to measure the hardness of the laminar rock chip embedded in the solid. In one embodiment, a Brinell hardness tester, model no. 206-02 0013, manufactured by Engineering Lab Equipment of Great Britain, is used although any suitable hardness tester may be used. The bottom surface of the plug is placed upon a hardness testing device support plate. Hardness testing device comprises a primary contact member commonly referred to as a ball indenter. The ball indenter is typically a sphere of one to three millimeters in diameter. The ball indenter contacts the contact surface portion of the laminar rock chip at the top surface so that force is applied by the ball indenter to the contact surface portion of the laminar rock chip in a vector which is within the laminar plane of the laminar rock chip so that a hardness of the laminar rock chip is measured. The contact surface portion of the laminar rock chip may be any portion of the exposed rock chip, the contact portion being that portion of the rock chip that is sufficiently exposed to be available for contact with the indenter of the hardness testing device. The contact surface portion may vary depending on the location of the rock chip on the hardness testing device support plate.

Figure 2:
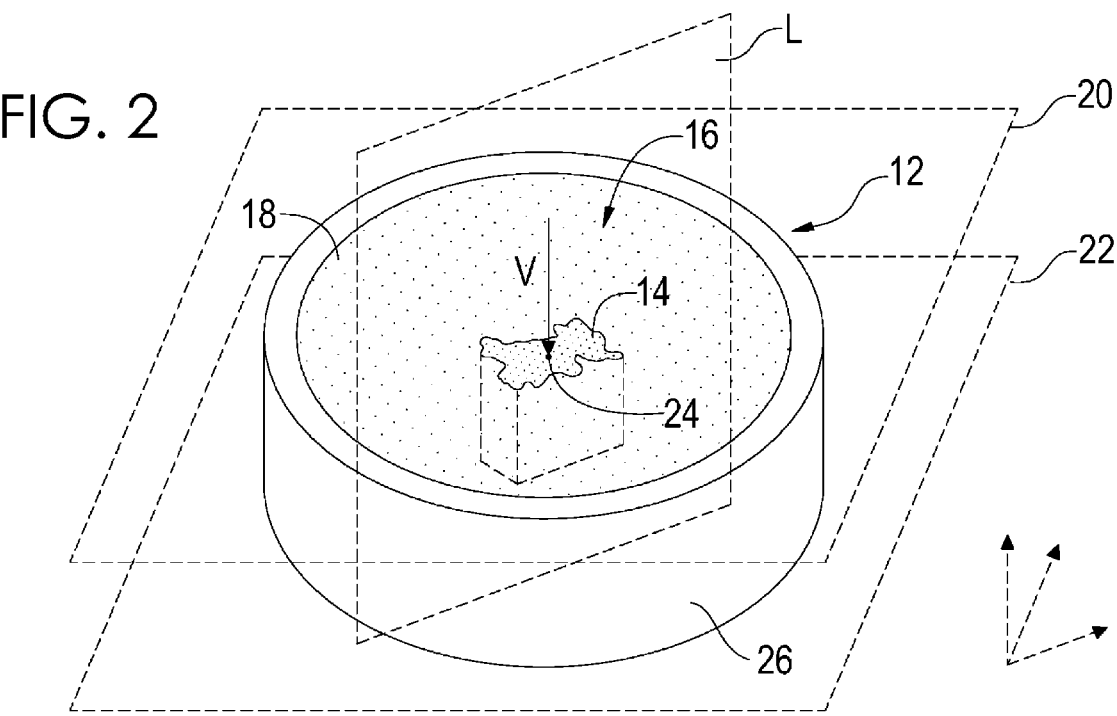
FIG. 2 is a perspective view of a plug, including a solid, a laminar rock chip, and a retention member consistent with one embodiment of the present invention In each of the above figures, like numerals are used to refer to like or functionally like parts among the several figures.

Turning now to the figures, FIGS. 1 and 2 illustrate a portion of a hardness tester 10 (FIG. 1 only) shown as a housing 11 and hardness tester support plate 28 and an article 12 comprising a plug 16 that includes a solid material 18 in the form of OSTALLOY® 158 metal alloy in which a laminar shale rock chip 14 is imbedded. Looking first at FIG. 2, article 12 comprises laminar rock chip 14 illustrated as a shale rock chip. Shale rock chip 14 is substantially surrounded by and imbedded within plug 16 comprised of solid material 18. Plug 16 forms a top planar surface 20 and a bottom planar surface 22 substantially parallel with top planar surface 20. Further illustrated in FIG. 2 is shale rock chip 14, wherein shale rock chip forms a contact surface portion 24 exposed at top planar surface 20 of plug 16. The laminar plane L of shale rock chip 14 is substantially perpendicular with top planar surface 20. FIG. 1 further illustrates plug 16 and retention member 26 disposed on hardness testing device support plate 28. A portion of the hardness tester 10 is shown, wherein the portion 10 illustrates the ball indenter 30, wherein the ball indenter and housing 11 are substantially perpendicular to top planar surface 20 of plug 16. Ball indenter 30 will be urged downward thereby contacting contact surface portion 24 of laminar rock chip 14 so that force is applied by ball indenter 30 to contact surface portion 24 of laminar rock chip 14 in a vector V which is within laminar plane L of laminar rock chip 14 so that a hardness of laminar rock chip 14 is measured. The hardness tester will typically assess hardness by measuring the Brinell hardness of the rock chip. Brinell hardness is defined as the ratio of the force applied to the rock chip divided by the area of contact made between the ball indenter and rock chip as defined by recommended practice, ASTM-E10.

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

The invention claimed is:

1. A method comprising
   disposing a retention member adjacent a planar surface, the retention member forming one or more inner side walls which, together with the planar surface, define a retention member void sized to receive a laminar rock chip;
   disposing the laminar rock chip in the retention member void such that a laminar plane of the laminar rock chip is substantially perpendicular to the plane of the planar surface;
   placing into the retention member void a flowable material capable of hardening, the flowable material flowing between a bottom surface of the laminar rock chip and the planar surface and further flowing around the laminar rock chip such that substantially all of the surface area of the laminar rock chip is covered by the flowable material;
   causing the flowable material to harden into a solid while retaining the laminar rock chip in place so that the laminar plane of the laminar rock chip remains substantially perpendicular to the plane of the planar surface, thereby forming a plug of solid material having the laminar rock chip embedded therein;
   removing the plug from the planar surface and abrading a top surface of the plug, the top surface and a bottom surface of the plug being substantially parallel to one another, and the top surface being sufficiently abraded so that a contact surface portion of the laminar rock chip is exposed at the top surface; and
   placing the bottom surface of the plug upon a hardness testing device support plate and contacting the contact surface portion of the laminar rock chip at the top surface with a primary contact member of the hardness testing device so that force is applied by the primary contact member to the contact surface portion of the laminar rock chip in a vector which is within the laminar plane of the laminar rock chip,
   so that a hardness of the laminar rock chip is measured.

2. A method according to claim 1 further comprising abrading the bottom surface of the plug so that the top surface of the plug is substantially parallel to the bottom surface of the plug.

3. A method according to claim 1 further comprising removing the plug from the retention member.

4. A method according to claim 1 wherein the flowable material comprises an epoxy.

5. A method according to claim 1 wherein the flowable material comprises a metal alloy.

6. A method according to claim 4 further comprising removing the plug from the retention member.

7. A method according to claim 1 further comprising disposing the laminar rock chip adjacent a stabilizing member, wherein the stabilizing member comprises at least one support member, wherein the support member retains the laminar rock chip such that the laminar plane of the laminar rock chip is substantially perpendicular to the plane of the planar surface.

8. An article comprising a laminar rock chip substantially surrounded by and imbedded within a plug comprised of a solid material, the plug forming a top planar surface and a bottom planar surface substantially parallel with the top planar surface, the laminar rock chip forming a contact surface portion exposed at the top planar surface of the plug, a laminar plane of the laminar rock chip being substantially perpendicular with the top planar surface.

9. The article according to claim 8, wherein the laminar rock chip is comprised of shale.

10. The article according to claim 9, wherein the solid material is either an epoxy or a metal alloy.

11. The article according to claim 10, wherein the solid material is a metal alloy having a melting point below 72° C.

12. The article according to claim 11, wherein the plug is further comprised of a solid retention member forming a perimeter of the plug.

13. The article according to claim 8, wherein the solid material is either an epoxy or a metal alloy.

14. The article according to claim 13, wherein the solid material is a metal alloy having a melting point below 72° C.

15. The article according to claim 8, wherein the plug is further comprised of a solid retention member forming a perimeter of the plug.

16. A method comprising
   disposing a retention member adjacent a planar surface, the retention member forming one or more inner side walls which, together with the planar surface, define a retention member void sized to receive a laminar rock chip;
   disposing the laminar rock chip in the retention member void;
   placing into the retention member void a flowable material capable of hardening, the flowable material flowing between a bottom surface of the laminar rock chip and the planar surface and further flowing around the laminar rock chip such that substantially all of the surface area of the laminar rock chip is covered by the flowable material;
   causing the flowable material to harden into a solid while retaining the laminar rock chip in place, thereby forming a plug of solid material having the laminar rock chip embedded therein;
   removing the plug from the planar surface and abrading a top surface of the plug, the top surface and a bottom surface of the plug being substantially parallel to one another, and the top surface being sufficiently abraded so that a contact surface portion of the laminar rock chip is exposed at the top surface; and
   placing the bottom surface of the plug upon a hardness testing device support plate and contacting the contact surface portion of the laminar rock chip at the top surface with a primary contact member of the hardness testing device so that force is applied by the primary contact member to the contact surface portion of the laminar rock chip,
   so that a hardness of the laminar rock chip is measured.

17. A method according to claim 16 further comprising abrading the bottom surface of the plug so that the top surface of the plug is substantially parallel to the bottom surface of the plug.

18. A method according to claim 16 further comprising removing the plug from the retention member.

19. A method according to claim 16 wherein the flowable material comprises an epoxy.

20. A method according to claim 16 wherein the flowable material comprises a metal alloy.

21. A method according to claim 19 further comprising removing the plug from the retention member.

22. An article comprising a laminar rock chip substantially surrounded by and imbedded within a plug comprised of a solid material, the plug forming a top planar surface and a bottom planar surface substantially parallel with the top planar surface, the laminar rock chip forming a contact surface portion exposed at the top planar surface of the plug.

23. The article according to claim 22, wherein the laminar rock chip is comprised of shale.

24. The article according to claim 23, wherein the solid material is either an epoxy or a metal alloy.

25. The article according to claim 24, wherein the solid material is a metal alloy having a melting point below 72° C.

26. The article according to claim 25, wherein the plug is further comprised of a solid retention member forming a perimeter of the plug.

27. The article according to claim 22, wherein the solid material is either an epoxy or a metal alloy.

28. The article according to claim 27, wherein the solid material is a metal alloy having a melting point below 72° C.

29. The article according to claim 22, wherein the plug is further comprised of a solid retention member forming a perimeter of the plug.

* * * * *